United States Patent [19]

Scaglione et al.

[11] Patent Number: 5,094,870

[45] Date of Patent: * Mar. 10, 1992

[54] CANINE BISCUITS CONTAINING AN INORGANIC PYROPHOSPHATE

[75] Inventors: Felice Scaglione, Hasbrouck Heights; Lorna C. Staples, Teaneck; John W. Ypma, Succasunna, all of N.J.

[73] Assignee: Nabisco Brands, Inc., Parsippany, N.J.

[*] Notice: The portion of the term of this patent subsequent to Mar. 19, 2008 has been disclaimed.

[21] Appl. No.: 653,396

[22] Filed: Feb. 11, 1991

Related U.S. Application Data

[62] Division of Ser. No. 358,150, May 30, 1989, Pat. No. 5,000,943.

[51] Int. Cl.$^5$ ............ A61K 7/20; A61K 7/16; A23L 1/30
[52] U.S. Cl. ............... 426/549; 424/442; 424/49; 424/57; 426/551; 426/805
[58] Field of Search ............ 426/549, 551, 805; 424/49, 57, 442

[56] References Cited

U.S. PATENT DOCUMENTS

| | | | |
|---|---|---|---|
| 2,870,017 | 1/1959 | Barch | 426/563 |
| 2,941,926 | 6/1960 | Salzmann et al. | 424/57 |
| 3,112,247 | 11/1963 | Schweizer | 424/52 |
| 3,137,632 | 6/1964 | Schiraldi | 424/49 |
| 3,194,738 | 7/1965 | Harrison et al. | 424/48 |
| 3,375,168 | 3/1968 | Curtin et al. | 424/57 |
| 3,442,604 | 5/1969 | Smith et al. | 424/57 |
| 3,488,419 | 1/1970 | McCune et al. | 424/49 |
| 3,507,796 | 4/1970 | Voss | 252/106 |
| 3,535,420 | 10/1970 | McCune et al. | 424/49 |
| 3,567,459 | 3/1971 | Wruk, III et al. | 426/72 |
| 3,639,569 | 2/1972 | Medcalf | 424/48 |
| 3,686,393 | 8/1972 | Woodruff et al. | 424/50 |
| 3,701,830 | 10/1972 | Welnrich et al. | 424/94 |
| 3,871,334 | 3/1975 | Axelrod | 119/29.5 |
| 3,882,257 | 5/1975 | Cagle | 426/274 |
| 3,899,607 | 8/1975 | Miller et al. | 426/805 |
| 3,927,201 | 12/1975 | Baines et al. | 424/54 |
| 3,934,002 | 1/1976 | Haefele | 424/54 |
| 3,942,537 | 3/1976 | Evers et al. | 131/278 |
| 3,956,479 | 5/1976 | Bauman | 424/54 |
| 3,957,964 | 5/1976 | Grimm, III | 424/10 |
| 3,959,458 | 5/1976 | Agricola et al. | 424/52 |
| 4,003,971 | 1/1977 | Mannara | 424/49 |
| 4,022,879 | 5/1977 | Dietrich | 424/49 |
| 4,044,158 | 8/1977 | Burkwall, Jr. | 426/271 |
| 4,145,447 | 3/1979 | Fisher et al. | 426/72 |
| 4,153,732 | 5/1979 | Muhler et al. | 426/72 |
| 4,215,149 | 7/1980 | Majlinger | 426/292 |
| 4,244,931 | 1/1981 | Jarvis et al. | 423/266 |
| 4,254,101 | 3/1981 | Denny, Jr. | 424/52 |
| 4,259,358 | 3/1981 | Duthie | 426/46 |
| 4,260,635 | 4/1981 | Fisher | 426/3 |
| 4,314,990 | 2/1982 | Denny, Jr. et al. | 424/52 |
| 4,323,551 | 4/1982 | Parran, Jr. | 424/54 |
| 4,364,925 | 12/1982 | Fisher | 424/50 |
| 4,419,372 | 12/1983 | Greene et al. | 426/635 |
| 4,421,527 | 12/1983 | Wason | 424/52 |
| 4,472,373 | 9/1984 | Ryan | 424/54 |
| 4,513,014 | 4/1985 | Edwards | 426/132 |
| 4,515,770 | 5/1985 | Besic | 424/49 |
| 4,515,772 | 5/1985 | Parran, Jr. et al. | 424/57 |
| 4,532,124 | 7/1985 | Pearce | 424/52 |
| 4,535,725 | 8/1985 | Fisher | 119/29 |
| 4,540,584 | 9/1985 | Someya | 424/144 |
| 4,557,219 | 12/1985 | Edwards | 119/29.5 |
| 4,590,066 | 5/1986 | Parran, Jr. et al. | 424/52 |
| 4,627,977 | 12/1986 | Gaffar et al. | 424/52 |
| 4,634,448 | 1/1987 | Ajioka et al. | 8/436 |
| 4,674,444 | 6/1987 | Axelrod | 119/29.5 |
| 4,678,662 | 7/1987 | Chan | 424/57 |
| 4,684,518 | 8/1987 | Parran, Jr. et al. | 424/52 |
| 4,702,929 | 10/1987 | Lehn et al. | 426/635 |
| 4,735,808 | 4/1988 | Scaglione et al. | 426/62 |
| 4,771,733 | 9/1988 | Axelrod | 119/29.5 |
| 4,772,461 | 9/1988 | Parran et al. | 424/52 |
| 4,795,655 | 1/1989 | Spiel et al. | 426/635 |
| 4,802,444 | 2/1989 | Markham et al. | 119/29 |
| 4,806,339 | 2/1989 | Parran et al. | 424/52 |
| 4,806,340 | 2/1989 | Gaffar et al. | 424/52 |
| 4,822,626 | 4/1989 | Spanier et al. | 426/94 |
| 4,869,898 | 9/1989 | Gaffar et al. | 424/52 |
| 4,880,619 | 11/1989 | Gaffar | 424/52 |
| 4,885,155 | 12/1989 | Parran et al. | 424/52 |
| 5,000,940 | 3/1991 | Staples et al. | 424/442 |
| 5,000,973 | 3/1991 | Scaglione et al. | 424/442 |

FOREIGN PATENT DOCUMENTS

| | | |
|---|---|---|
| 168071 | 12/1953 | Australia . |
| 1233121 | 2/1988 | Canada . |
| 079611 | 5/1983 | European Pat. Off. . |
| 0097476 | 1/1984 | European Pat. Off. . |
| 0236290 | 9/1987 | European Pat. Off. . |
| 0236827 | 9/1987 | European Pat. Off. . |
| 0249398 | 12/1987 | European Pat. Off. . |
| 0251591 | 1/1988 | European Pat. Off. . |
| 0254452 | 1/1988 | European Pat. Off. . |
| 0288909 | 11/1988 | European Pat. Off. . |
| 0291747 | 11/1988 | European Pat. Off. . |
| 0295116 | 12/1988 | European Pat. Off. . |

(List continued on next page.)

OTHER PUBLICATIONS

"Nutritional Requirements of Domestic Animals", The Natl. Res. Council of the Natl. Acad. of Sciences, (Rev. 1974), Nutrient Requirements of Dogs, pp. 9-11, 13, 14 and 35.
Chemical Abstracts 89: 74468t (1978).
Chemical Abstracts 83: 57001u (1975).
Phosphoric Acid and Phosphates, Encyclopedia of Chemical Technology, Kirk-Othmer, 3rd Ed. (1982), vol. 17, pp. 426 to 472.

Primary Examiner—Ronald W. Griffin

[57] ABSTRACT

Process for preparing dog biscuits which contain at least one inorganic pyrophosphate salt. The dog biscuits containing at least one inorganic pyrophosphate salt are chewed and/or eaten by dogs, with the result that tartar accumulations on their teeth are reduced or prevented.

15 Claims, No Drawings

| FOREIGN PATENT DOCUMENTS | | |
|---|---|---|
| 0297211 | 1/1989 | European Pat. Off. |
| 0297212 | 1/1989 | European Pat. Off. |
| 0297213 | 1/1989 | European Pat. Off. |
| 305283 | 3/1989 | European Pat. Off. |
| 0309414 | 3/1989 | European Pat. Off. |
| 0311412 | 4/1989 | European Pat. Off. |
| 0316079 | 5/1989 | European Pat. Off. |
| 0319516 | 6/1989 | European Pat. Off. |
| 2749581 | 5/1978 | Fed. Rep. of Germany. |
| 3041237 | 6/1982 | Fed. Rep. of Germany. |
| 86-03674 | 7/1986 | PCT Int'l Appl. |
| 777556 | 6/1957 | United Kingdom. |
| 1179343 | 1/1970 | United Kingdom. |
| 1386627 | 3/1973 | United Kingdom. |
| 2092000 | 8/1982 | United Kingdom. |
| 2109686 | 6/1983 | United Kingdom. |
| 2180157 | 3/1987 | United Kingdom. |
| 2182244 | 5/1987 | United Kingdom. |
| 2188548 | 10/1987 | United Kingdom. |
| 2191500 | 12/1987 | United Kingdom. |
| 2194426 | 3/1988 | United Kingdom. |
| 2200551 | 8/1988 | United Kingdom. |
| 2201593 | 9/1988 | United Kingdom. |
| 2204487 | 11/1988 | United Kingdom. |
| 2206027 | 12/1988 | United Kingdom. |

CANINE BISCUITS CONTAINING AN INORGANIC PYROPHOSPHATE

This is a division of Ser. No. 358,150, filed on May 30, 1989, of Scaglione et al., now U.S. Pat. No. 5,000,943, issued on Mar. 19, 1991.

BACKGROUND OF THE ART

1. Field Of The Invention

The invention relates to canine biscuits containing an anti-tartar agent. The invention also relates to a process of preparing such canine biscuits. The invention further relates to a process of preventing tartar formation on dogs' teeth by the dog chewing on and eating such canine biscuits.

2. Background Art

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars. Maturel calculus consists of an inorganic portion which is largely calcium phosphate arranged in a hydroxylapatite crystal lattice structure similar to one, enamel and dentine. An organic portion is also present and consists of desquamated epithelial cells, leukocytes, salivary sediment, food debris and various types of microorganisms. As the mature calculus develops, it becomes visibly white or yellowish in color unless stained or discolored by some extraneous agency. In addition to being unsightly and undesirable from an aesthetic standpoint, the mature calculus deposits are constant sources of irritation of the gingiva and thereby are a contributing factor to gingivitis and other diseases of the supporting structures of the teeth, the irritation decreasing the resistance of tissues to endogeneous and exogenous organisms.

A wide variety of chemical and biological agents have been suggested in the art to retard calculus formation or to remove calculus after it is formed in humans. Mechanical removal of this material is done routinely in humans.

German Patent No. 3,426,203 discloses a chewing article for dogs consisting of 92 vol. parts of raw skin, 4 vol. parts of lime and 4 vol. parts of feed salts mixture containing (per 100 g) 700 mg of potassium, 1500 mg of carbonate, 1000 mg of calcium, 110 mg of phosphate, 40 mg of iron and 1 mg of iodine. The article is prepared from cow skin by stripping the skin, and subjecting the subcutaneous material to neutralization to pH 6, treating with a solution of iodine-containing feed salt and lime, shaping to form the article and drying.

U.S. Pat. No. 4,145,447 discloses a hard, unit-integral, unitized, self-contained, compact, chew-resistant nutritionally balanced animal food product 3 final having a density of at least about 0.5 oz./in.$^3$, a final water content of at least about 5.5 percent by weight, and a breaking force of at least about 60 psi. The animal food contains, for example, dried meals, dried fish, dried dairy products, fish meal, fish flour, cereals, flours, carbohydrates, dried fruits, etc., with or without food additives or supplements such as vitamins, minerals, medicinals, etc., for example chemicals, enzymes, etc., capable of removing plaque or tartar from the animals's teeth, etc.

U.S. Pat. No. 4,044,158 discloses the use of tetrasodium pyrophosphate as a chelating agent in semi-moist pet foods. The neutral chelating agent is used in a semi-moist pet food having a pH of from 6.3 to 7.2 and which comprises about 5 to about 50 percent by weight meat or meat by-products, about 15 to about 50 percent moisture, and about 1 percent to about 26 percent by weight vegetable protein. The vegetable protein, an amylaceous material, and the chelating agent, it is taught, forms a composition which replaces part of the caseinate binder customarily present in a semi-moist pet food. No mention is made of any anti-tartar effectiveness of the pet food.

U.S. Pat. No. 4,215,149 discloses a process for maintaining the palatability of a pet food by coating particulates having a moisture content of less than 15 percent with fat and then with a monoalkali metal or monoalkaline earth metal salt of phosphoric acid to make the food more palatable to cats. Exemplary salts are monosodium phosphate and monocalcium phosphate.

U.S. Pat. No. 3,639,569 discloses the use of a tris-(phosphonoalkyl)amine in a dentifrice composition with a dentifrice abrasive selected from the group consisting of beta-phase calcium pyrophosphate, particulate thermosetting polymerized resin, alumina, sodium metaphosphate, and mixture thereof, or in a mouthwash composition, or in a chewing gum composition or dental prophylaxis paste composition. The patent discloses that the use of inorganic pyrophosphates as anti-calculus agents in oral compositions has the problem of hydrolysis in aqueous products and loss of activity prior to the termination of the normal shelf-life of such products. The patent also teaches that calculus inhibition by chelation of calcium ion may seriously damage tooth structure by decalcification.

U.S. Pat. No. 3,957,964 discloses microcapsules containing essential oils of mint flavor in a dentifrice adapted to release a plural flavor-burst signaling the onset of and the completion of a toothbrushing operation. The dentifrice may be a toothpaste having dicalcium phosphate as a polishing agent.

U.S. Pat. No. 3,959,458 discloses the use of from about 0.2 to about 8 percent by weight of an orally acceptable monofluorophosphate with an anticalculus agent which is a condensation product of ammonia and phosphorus pentoxide or with a polyphosphonate in an oral composition. The oral composition may further contain a calcium pyrophosphate abrasive. The patent teaches that sodium or calcium monofluorophosphate, when used in combination with the anticalculus agents, exhibit no detectable damage to silicate fillings in the mouth whereas other anticaries agents, such as sodium fluoride, do exhibit damage. It is also taught that below about pH 5.0 some of the anticalculus agents can damage dental enamel.

U.S. Pat. No. 4,314,990 discloses the use of a phosphate buffering agent, which provides phosphate ions to maintain the pH of a slurry in the range of about 6.8 to 8.0, in a toothpaste composition which comprises 6 to 45 percent of a silica dental abrasive, from about 0.01 to 3 percent of a fluoride ion source, from about 10 to 45 percent of water, and about 30 to 70 percent of a humectant.

U.S. Pat. No. 4,323,551 discloses the use of a tetraalkali metal pyrophosphate salt to provide from about 0.5 to 5 percent of the $P_2O_7$ species in a mouthwash composition comprising 0.02 to 0.2 percent of a quaternary ammonium compound, and a carrier liquid wherein the pH is adjusted to about 7.0 to 9.5 with a mineral or organic acid.

U.S. Pat. No. 4,421,527 discloses the use of a precipitated amorphous silicon dioxide prepared by acidulation in an abrasive composition in a toothpaste that contains fluoride. Phosphoric acid is disclosed as an acidulant. Soluble phosphates, such as the pyrophosphates, are taught as improving fluoride pellicle penetration.

U.S. Pat. No. 4,515,770 discloses a process wherein a soluble source of phosphate ions or a soluble source of calcium ions is uniformly distributed through sucrose in crystalline form as a result of dissolution of the sucrose and soluble source of calcium or phosphate ions in water followed by evaporation of the water solvent. It is taught that it is of substantial importance that the calcium or phosphate ion source be as rapidly soluble in saliva as the sugar so that the protective ions will migrate to salivary retention areas as rapidly as the sugar. A material, it is taught, which is cariogenic by virtue of directly or indirectly participating in the lowering of pH in salivary retention areas is rendered non-cariogenic by treatment to incorporate enough of either a calcium or phosphate ion source to keep the acidic medium from dissolving the tooth enamel. It is also disclosed that systematically administered phosphates are said to differ in cariostatic activity depending on the type of anion (cyclictrimeta-, hexameta-, ortho-, and pyrophosphate, increasing in effectiveness in that order). It is further taught that these developments have unfortunately resulted in only minor advances in prevention of carious degradation of teeth because none of the "remineralization" processes have been shown to be consistently effective.

U.S. Pat. No. 4,515,772 discloses the use of from about 10 to about 70 percent of a dental abrasive selected from the group consisting of insoluble metaphosphates, alumina, thermosetting polymerized resins, and silica from about 50 ppm to about 3,500 ppm of fluoride ions from a fluoride ion source, and an amount of a pyrophosphate salt selected from the group consisting of dialkali metal and mixtures of dialkali metal and tetraalkali metal pyrophosphate salts sufficient to provide at least 1.5 percent $P_2O_7$. The pyrophosphate ion is provided by a $P_2O_7$ mixture of disodium pyrophosphate and tetrasodium pyrophosphate. The fluoride ion source is disclosed as an essential component. The upper limits on the sodium pyrophosphate salts are determined by solubility considerations, while the tetrapotassium level is established for taste reasons. It is further taught that surprisingly mixtures of certain pyrophosphate salts can provide a safe and effective anticalculus product while also not presenting difficult formulation problems.

U.S. Pat. No. 4,532,124 discloses the use of a plaque mineralizing aqueous solution comprising urea, a fluoride salt, a water-soluble calcium salt, and a water-soluble phosphate salt in the mineralization of dental plaque. It is disclosed that high plaque calcium and inorganic phosphate levels will lower the critical pH, that is, the pH which plaque must reach before it becomes unsaturated with respect to biological apatite, and enamel dissolution commences. The urea is metabolized by bacteria to produce alkali in plaque. Aspartame and amino acids may be substituted for urea.

U.S. Pat. No. 4,540,584 discloses the use of coral sand as an effective component in a mineral supplement in an amount sufficient to provide calcium carbonate as a mineral supplemental for humans, such coral sand also containing $PO_4$. The composition, it is taught, is useful for replenishing calcium and phosphorous, as well as other minerals. Acidic foods tend to result in decayed teeth and bone fractures because of calcium poverty.

U.S. Pat. No. 3,567,459 discloses conversion of a hot melt of sugar having a moisture content less than 5 percent to a dough-like bone-forming composition by incorporation of nutritional fillers, fatty flavoring materials, and fat-absorbing farinaceous materials. The composition is formed and cooled. The patent teaches mastication of bones provides teeth cleaning benefits stemming from abrasion and other contacts of bone fragments.

U.S. Pat. No. 3,701,830 discloses the use of a neutral protease enzyme for removing plaque from and preventing the formation of calculus on the teeth of dogs wherein the neutral protease is obtained by fermentation with a strain of Bacillus suptilis or Bacillus sterothermophilus.

U.S. Pat. No. 3,882,257 discloses a process where 75 percent by weight of bones is admixed with 23.5 percent by weight of animal by-products, and the mixture is bound with salt in the preparation of a pet food having about 40 percent natural animal protein. The product enables a dog to exercise his jaws and gums to remove tartar from teeth.

U.S. Pat. No. 3,899,607 discloses a dough mixture which is: worked and shaped at a temperature of 170° to 220° F. to form a simulated bone having a structural matrix; or cooked, dried to a moisture content of between 5 and 12 percent by weight, ground and mixed with a dextrin adhesive to form a simulated bone having a structural matrix.

U.S. Pat. No. 4,364,925 discloses an enzyme for removing plaque and/or tartar from the teeth is included in a chew-resistant layer of an integral chew-resistant multi-layer animal food system having a structure supporting fibers. A cracker containing protease or amylase. U.S. Pat. Nos. 3,194,738 and 3,686,393 also relate to the use of enzymes for inhibiting plaque.

U.S. Pat. No. 3,488,419 discloses the use of a polyphosphonate or salt thereof in an oral composition or toothpaste. The patent teaches that inorganic polyphosphates, such as pyrophosphates, hydrolyze in aqueous products and do not remain in active form throughout the normal shelf-life of such products. The patent also teaches that calculus inhibition by chelation of calcium ion may seriously damage tooth structure by decalcification.

U.S. Pat. No. 3,535,420 discloses the use of a cyclic tetraphosphonic acid as an anti-calculus agent in an oral composition. The patent teaches that inorganic polyphosphates, such as pyrophosphates, hydrolyze in aqueous products and do not remain in active form throughout the normal shelf-life of such products. It is also taught that although certain of the art-disclosed chelators are purportedly safe for use on dental enamel, the chemical similarity of calculus to the tooth structure limits the usefulness of the chelation approach because the more effective chelators can seriously damage the tooth structure by decalcification. The cyclic tetraphosphonates are calcium sequestrants, but they retard calculus formation by a mechanism that is believed to involve the inhibition of hydroxylapatite crystal growth rather than calcium sequestering.

U.S. Pat. No. 3,686,393 discloses the use of a dextranase used to eliminate dental plaque formation.

U.S. Pat. No. 3,956,479 discloses the use of a quaternary ammonium compound having a carbamate, or a thiocarbamate, or a dithiocarbamate, or a carbamide group in an oral preparation. The compounds, it is taught, are effective in reducing caries and inhibiting formation of oral calculus.

U.S. Pat. No. 4,003,971 discloses the use of a dentifrice component in the production of dentifrice speckles. Antimicrobial agents for incorporation into oral dentifrice formulations may be effective by reducing dental plaque or inhibiting the formation of dental calculus.

U.S. Pat. No. 4,254,101 discloses the use of from about 6 to 45 percent of a silica dental abrasive, from about 30 to 70 percent of a humectant, and from about 0.03 to 1.0 percent of a carboxyvinyl polymer in a toothpaste composition. The use of optional anticalculus agents, in amounts of from about 0.01 to 2.5 percent by weight of the toothpaste composition are taught.

U.S. Pat. No. 4,472,373 discloses the use of a pyridium salt as an anti-plaque agent in a flavored alcoholic carrier. Phosphates, such as calcium pyrophosphate, are disclosed as dentifrice abrasives.

U.S. Pat. No. 4,153,732 discloses the use of at least one soluble aluminum ion containing salt with adipic acid, ascorbic acid, or mixtures thereof as a cariostatic additive for comestibles. The patent teaches that calcium pyrophosphate and insoluble sodium metaphosphate abrasives coact with aluminum fluoride in dentifrice compositions.

U.S. Pat. No. 4,627,977 discloses an oral composition, such as, a toothpaste (including gel or cream), mouthwash, lozenge, chewing gum or tooth powder, containing a calculus-inhibiting amount of a linear molecularly dehydrated polyphosphate salt (e.g., a water-soluble alkali metal pyrophosphate) to inhibit enzymatic hydrolysis of said polyphosphate salt in saliva, a combination of a fluoride ion-providing source and a synthetic linear polymeric polycarboxylate. See also British Published Patent Application No. 2,180,157.

U.S. Pat. No. 4,678,662 discloses calcium carbonate particles coated with at least one pyrophosphate derivative, such as, disodium dihydrogen pyrophosphate and tetrasodium pyrophosphate.

European Published Patent Application No. 0236920 discloses a dentifrice comprising essentially insoluble calcium pyrophosphate as an abrasive and a clinically effective amount of soluble pyrophosphate, such as, tetrasodium pyrophosphate, or tripolyphosphate as an anticalculus agent.

U.S. Pat. No. 4,684,518 discloses a process for reducing the incidence of calculus on dental enamel. The enamel surfaces in the mouth are contacted with a composition comprising a soluble pyrophosphate source capable of providing at least 1.5 percent of $P_2O_7$ and from about 50 to about 3500 ppm of fluorine.

U.S. Pat. No. 4,722,461 discloses an oral composition in the form of a mouthwash or liquid dentifrice comprising: an amount of a fluoride ion source sufficient to supply from about 50 ppm to about 3500 ppm of fluoride ions; an amount of a pyrophosphate salt selected from the group consisting of dialkali metal and mixtures of dialkali metal and tetra-alkali metal pyrophosphate salts sufficient to provide at least 1.5 percent of $P_2O_7$; and water. The pH of the composition is from about 6.0 to about 10.0. Calcium pyrophosphate is termed to be an abrasive. See European Published Patent Application No. 0097476.

British Published Patent Application No. 2,201,593 discloses an oral composition in the form of a toothpaste effective in reducing calculus comprising: a safe and effective amount of a soluble pyrophosphate salt or mixture of the salts; from about 5 to about 60 percent of a suitable toothpaste abrasive; an amount of a fluoride ion source sufficient to provide from about 50 ppm to about 3500 ppm fluoride; from about 5 to about 60 percent of humectant selected from the group consisting of sorbitol, glycerine, polyethylene glycols, mineral oil, and mixtures thereof; from about 0.3 to about 5 percent of a surfactant selected from the group consisting of alkyl sulfate surfactants, ethoxylated alkyl sulfate surfactants and mixtures thereof; and water. The composition has a pH of from about 6 to about 10, is substantially free of polyethylene glycols having fewer than six ethoxy units and short chain monohydric alcohols and has potassium ions present at a level of from about 0.5 to about 7 percent. The soluble pyrophosphate salt can be, for example tetrapotassium pyrophosphate, tetrasodium pyrophosphate, sodium acid pyrophosphate and mixtures thereof.

U.S. Pat. No. 4,806,340 discloses an oral dentifrice composition such as a toothpaste, dental gel, toothpowder, dental tablet or lozenge containing as anticalculus agent about 4.3 to about 7 percent of alkali metal pyrophosphates comprising at least 4.3 percent of tetrapotassium pyrophosphate alone or admixed with up to 2.7 percent of tetrasodium pyrophosphate, and as inhibitors against enzymatic hydrolysis of such agent in saliva, a fluoride and preferably up to about 3 percent of a synthetic anionic polymeric polycarboxylate. The composition is used in a program of oral hygiene and/or for inhibiting dental calculus. It is known that saliva contains acid phosphatase, alkaline phosphatase and pyrophosphatase enzymes. It is considered that any one off the three enzymes may adversely affect pyrophosphates as an inhibitor of hydroxyapatite formation and calculus. It is accordingly apparent that an anticalculus pyrophosphate dentifrice composition, should inhibit, reduce or nullify the destructive activity of all three salivary enzymes. See Also British Published Patent Application No. 2,182,244.

Australian Published Patent Application No. 168071 discloses a dialkali metal-alkaline earth metal pyrophosphate containing about 1 to about 5 percent by weight of chemically combined fluorine. The composition is a dentifrice base. The method of producing the fluorinated dialkali metal-alkaline earth metal pyrophosphate, which comprises reacting together, in the presence of an aqueous medium, a water-soluble metal fluoride, an alkali metal pyrophosphate (such as, tetrasodium pyrophosphate), and a water soluble alkaline earth metal salt. The reactants being employed in the proportions required to yield a dialkali metal-alkaline earth metal pyrophosphate containing about 1 to about 5 percent by weight of chemically combined fluorine.

British Patent No. 777,556 discloses a dentifrice composition which contains a fluoride compound which releases fluoride ions in water, a calcium polyphosphate polishing agent, and a calcium ion suppression agent to maintain the effect of the fluoride upon ageing.

U.S. Pat. No. 4,822,626 discloses a process of producing a biscuit with a baked-on proteinaceous coating. The process includes preparing a dough piece from a dough comprising flour, meal, fat and water; and enrobing the dough piece with a viscous coating formation comprising 10 to 30 weight percent of a dextrin carrier, 10 to 50 weight percent of meat, 10 to 30 weight percent of a glazing agent, 1 to 5 weight percent of polysaccharide gum, 5 to 15 weight percent of a monosaccharide sugar, 5 to 15 weight percent of a disaccharide sugar, and water, all based upon the total dry solids. The dough piece is baked to form a dry biscuit with a baked-on coating. The glazing agent can comprise a gelatin or a modified food starch, and the polysaccharide gum can be a xanthan gum. Biscuits produced by the process and a bakable proteinaceous coating formulation as employed in step (b) are disclosed.

BROAD DESCRIPTION OF THE INVENTION

An object of the invention is to provide dry animal biscuits containing pyrophosphate, particularly dog biscuits containing pyrophosphate. Another object of the invention is to provide a process for preparing dog biscuits containing pyrophosphate. Another object of the invention is to provide a process for the prevention of tartar accumulation on the teeth of dogs. A further object of the invention is to provide a process for the prevention of tartar accumulation on the teeth of dogs by the chewing and eating of dog biscuits containing pyrophosphate by the dogs. Other objects and advantages of the invention are set out herein or are obvious herefrom to one skilled in the art.

The objects and advantages of the invention are achieved by the compositions and processes of the invention.

The invention involves a process for preparing dog biscuit dough which contains at least one inorganic pyrophosphate. The process includes admixing the ingredients of the biscuit dough and the at least one inorganic pyrophosphate. The inorganic pyrophosphate also reduces the accumulation of tartar on the teeth of dogs.

Tartar is an incrustation of the teeth consisting of salivary secretion, food residue and various salts, such as, calcium carbonate or phosphate. Tartar is also termed dental calculus.

Caries are cavities or decay of the teeth which begins at the surface of the tooth and may progress through the dentine into the pulp cavity. It is believed that the action of microorganisms in the mouth on ingested sugars and carbohydrates produces acids that eat away the enamel. By preventing the formation of calculus or tartar, the invention formulation is in effect an anti-cariogenic agent.

Preferably the dry dough ingredients and the inorganic pyrophosphate salts are mixed, then water is added and the mixing continued, and finally the fat (tallow) is added and thoroughly mixed in.

The dog biscuits can be made from any suitable dough. In one advantageous embodiment, a bone-shaped canine biscuit is provided which is baked from a dough comprising wheat flour, wheat meal, soybean meal, meat and bone meals, animal fat and water.

The dog biscuit dough preferably contains about 0.1 to about 10 weight percent of the at least one inorganic pyrophosphate compound, and most preferably about 0.5 to about 5 weight percent of said at least one inorganic pyrophosphate compound. The preferred inorganic pyrophosphate salt(s) is an alkali metal pyrophosphate. While the preferred alkali metal pyrophosphate is tetrasodium pyrophosphate, the most preferably the dog biscuit dough contains a combination of sodium acid pyrophosphate and tetrapotassium pyrophosphate (or tetrasodium pyrophosphate).

The invention also involves a process for preparing unbaked dog biscuits from the dog biscuit dough. The invention also involves unbaked dog biscuits which contain at least one inorganic pyrophosphate. The dog biscuit pieces preferably are bone shaped. The unbaked dog biscuits preferably have a moisture content usually in the range of about 25 to about 40 weight percent, preferably about 33 to about 35 weight percent.

The invention also involves a process for preparing baked dog biscuits which contain at least one inorganic pyrophosphate. The process includes:

(a) shaping a dog biscuit dough, which contains the at least one inorganic pyrophosphate, into dog biscuit pieces comprising unbaked dog biscuits; and (b) baking the unbaked dog biscuits. The baked dog biscuits can be dried, if necessary, to obtain the desired moisture level. The baked dog biscuits should have a moisture content of 13 weight percent or less, advantageously between about 5 and 13 weight percent, preferably between about 8 and about 12 weight percent.

The invention product is baked so that it comprises a baked dog biscuit which contains at least one inorganic pyrophosphate.

The invention further involves baked dog biscuits which contain at least one inorganic pyrophosphate. The ingredients, ratios, ranges, etc., for the invention dog biscuit dough applies to the invention baked dog biscuits, except as otherwise noted herein.

The invention product preferably should be slightly acid to neutral.

The inorganic pyrophosphates are anti-tartar, anti-plaque or anti-calculus agents. The invention product exhibits anti-tartar properties over its normal shelf life. The invention product does not adversely affect canine tooth enamel.

The invention further involves a process for the prevention or reduction of tartar accumulation on the teeth of dogs. The process includes the chewing and/or eating of the invention baked dog biscuits by the dogs. (The term "dog biscuit" herein means a baked dog biscuit unless otherwise stated herein or otherwise obvious herefrom to one skilled in the art.)

The invention biscuits, when eaten and chewed by dogs, cleans tooth surfaces, removes tartar (by mechanical action), and exercises and massages the gums. The pyrophosphate in the invention biscuits prevents or reduces the formation of tartar on the dog's teeth. The pyrophosphate, in the levels involved, does not adversely affect the gastrointestinal system or the health of the dogs.

DETAILED DESCRIPTION OF THE INVENTION

As used herein, all parts, percentages, ratios and proportions are on a weight basis unless otherwise stated herein or otherwise obvious herefrom to one skilled in the art. As used herein, all temperatures are in degrees Fahrenheit unless otherwise stated herein or otherwise obvious herefrom to one skilled in the art.

The dog biscuits containing pyrophosphate can be made from any suitable dough.

Any suitable dough comprising at least one flour, meal, fat and water can be employed for the product. For instance, when the desired product is a canine biscuit, a conventional dough for dog biscuits can be used, optionally containing discrete particles of meat and/or meat byproducts or farinaceous material. Such doughs typically contain fat solids. Examples of suitable doughs for the production of hard dog biscuits are disclosed in U.S. Pat. No. 4,454,163, and suitable doughs for the production of soft dog biscuits (containing humectant to control water activity) are disclosed in U.S. Pat. No. 4,454,164. The pertinent portions of U.S. Pat. Nos. 4,454,163 and 4,454,164 are incorporated herein by reference. Particulate proteinaceous particles, such as particles of meat, texturized vegetable protein and/or meat byproducts can be incorporated to add flavor to the biscuits and texturize the surface. Particulate farinaceous materials such as bran particles can also be employed to texturize the interior and/or surface of the biscuits and to provide other useful properties to the product. A dough found to produce biscuits highly palatable to dogs includes suitable proportions of wheat flour, wheat meal, soybean meal, meat and bone meal, animal fat and natural flavors in admixture with water. The meal used in the doughs suitable for production of biscuits useful in the invention can comprise meat and/or bone and/or vegetable matter including farinaceous materials, materials prepared from legumes such as beans and peas, tuberous materials such as potato meal, and the like. The meals can be finely or coarsely ground as desired for the texture. Flours made from any suitable farinaceous material can be used.

The doughs generally have a water activity of about 0.90 and above upon completion of mixing of the dough ingredients. A suitable dough contains farinaceous material, an edible oil, an antioxidant, an antimycotic, salt, animal fat, added vitamins and minerals, such as those disclosed in U.S. Pat. No. 4,229,485, column 5, lines 7 to 57, which is incorporated herein by reference. The compositions of the invention also preferably contain at least one animal-derived proteinaceous meal such as meat meal, bone meal and fish meal. A good biscuit dough for producing the biscuits of the invention contains about 50 to 60 percent by weight wheat flour, about 5 to 10 percent by weight soybean meal, about 3 to 10 percent by weight meat and bone meal, about 1 to 5 percent wheat meal, about 1 to 5 percent animal fat preserved with BHA, about 20 to 30 percent by weight water, and about 2 to 5 percent by weight of natural flavors, vitamin and mineral preblend, and acidulant.

The solvent used in preparing the dog biscuit dough, or for incorporating certain ingredients therein, is most preferably water, but other non-toxic, edible solvents, such as, ethanol or ethanol/water, can be used. The problem of the necessity of solvent removal from the dough due to toxicity is to be avoided in most cases. If a mixture of ethanol and water is used, the amount of ethanol in the mixture is generally about 5 to about 60 percent, preferably about 5 to about 25 percent. When one or more of the inorganic pyrophosphates is not water soluble, it may be ethanol soluble. It may be necessary to use a non-aqueous solvent, or mixture of water therewith, to incorporate the inorganic pyrophosphate.

The invention includes the use of at least one inorganic pyrophosphate. Preferably the inorganic pyrophosphates are water soluble or preferably a mixture of water soluble and water insoluble inorganic pyrophosphates are used. Such a mixture is usually used to provide a desired pH. The use of water-insoluble or difficultly soluble inorganic pyrophosphates in a dog biscuit dough is not a significant problem compared to use of such materials in a solution, such as, a mouth wash.

The pH of the dough can be adjusted using an inorganic base (e.g., KOH, NaOH, CaOH, LiOH, MgOH, etc.) or an inorganic acid (e.g., $H_2SO_4$, HCl, etc.), but this approach has the disadvantages of possibly causing a misbalance or overabundance of one or more chemical entities and possibly introducing unwanted salts.

Generally 0.1 to 10 weight percent, advantageously about 0.5 to about 5 weight percent, of inorganic pyrophosphate is used.

When a mixture of tetrasodium pyrophosphate (TSPP) and sodium acid pyrophosphate in aqueous solution at the 5 weight percent level was incorporated in dog biscuit dough, there was reduced dough gluten development; the dog biscuits were bleached (whitish) and crumbly; and the dog biscuits were softer (a hardness problem) than the control dog biscuits. At the level of 3 weight percent of a mixture of tetrasodium pyrophosphate and sodium acid pyrophosphate, the same problems occurred, but less severely. The addition of the inorganic pyrophosphates in dry form to the dry ingredients in the dough preparation basically eliminated the above problems. It was also found that better results were secured by using the inorganic phosphates in powder form as opposed to granular form.

The inorganic pyrophosphates are preferably alkali metal pyrophosphates. The preferred alkali metal pyrophosphates are tetrasodium pyrophosphate and tetropotassium pyrophosphate. An example of a useful tetraalkali metal pyrophosphate is tetralithium pyrophosphate. Alkaline earth metal pyrophosphates are also useful, but they are generally insoluble in water. Preferably, the inorganic pyrophosphates are soluble in water.

Kirk & Othmer, "Encyclopedia Of Chemical Technology", 2nd Ed., Vol. 15, (1965), pages 232 to 276, discloses a number of water-soluble inorganic pyrophosphate salts. The pertinent portions of Kirk & Othmer, "Encyclopedia Of Chemical Technology", 2nd Ed., Vol. 15, (1965), pages 232 to 276, are incorporated herein by reference.

Examples of dialkaline metal pyrophosphates are dicalcium pyrophosphate, dibarium pyrophosphate and dimagnesium pyrophosphate. Trialkali metal monoacid pyrophosphates, such as, trisodium hydrogen pyrophosphate, can be used. Monoalkali metal triacid pyrophosphates, such as, sodium trihydrogen pyrophosphate, can also be present in limited amounts. Examples of other inorganic pyrophosphates include manganese pyrophosphate and dizinc pyrophosphate.

The formula $M_{n+2}P_nO_{3n+1}$, where M is a univalent metal, is the formula for univalent metal pyrophosphates when n is 2. The formula $M'_nP_nO_{3n+1}$, where M' is a divalent metal, is the formula for divalent metal pyrophosphates when n is 2. Such univalent metal pyrophosphates and divalent metal pyrophosphates can be used in the invention. Polyphosphates have the formula $M_{m+2}P_mO_{3m+1}$ or $M'_nP_2O_{3n+1}$, where n is 2, 3, 4, 5, . . . , and the oxide ratio R between the cationic oxides ($M_2O$ or M'O) and anionic oxides ($P_2O_5$) is between 1 and 2. The oxide ratio for pyrophosphate is 2.

Tetrasodium pyrophosphate, one part, is soluble in 13 parts of cold water and in 2.5 parts of boiling water. It is insoluble in ethanol. Dicalcium pyrophosphate is practically insoluble in water. The invention use of the term "solution" includes slurries, suspensions and the like. Tetrapotassium pyrophosphate is freely soluble in water and is insoluble in ethanol.

Advantageously a mixture of water-soluble tetrasodium pyrophosphate or tetrapotassium pyrophosphate and water-insoluble dicalcium pyrophosphate is used (in a ratio to achieve the desired pH). Most preferably a mixture of sodium acid pyrophosphate and tetrapotassium pyrophosphate is used (in a ratio to achieve the desired pH). In such most preferred mixture, tetrasodium pyrophosphate is not used as it would provide too much sodium in the composition.

The maximum allowable GRAS level in a composition for sodium acid pyrophosphate (SAPP) is 2.1 weight percent and tetrapotassium pyrophosphate (TKPP) is 1.4 weight percent in baked goods. If GRAS levels change (rise) or if higher levels are allowed by the regulatory agencies, higher levels can be used in the invention. TKPP delivers approximately 52.65 percent of $P_2O_7$; SAPP delivers about 78.36 percent of $P_2O_7$; and TSPP delivers about 65.4 percent of $P_2O_7$.

The most preferred invention dough contains trisodium monoacid pyrophosphate (that is, sodium acid pyrophosphate or SAPP) and tetrapotassium pyrophosphate in a weight ratio of about 60 to about 40.

The pyrophosphate(s) is used in sufficient amount to deliver generally from about 0.1 to about 5, preferably from about 0.5 to about 3.5, most preferably 1.4 to 2.5 weight percent (based on the total composition), of $P_2O_7$.

A study of the application of aqueous solutions of a mixture of tetrasodium pyrophosphate and sodium acid pyrophosphate to the teeth of dogs by spraying for one month resulted in dose response data. The aqueous solutions containing 5 and 3 weight percent of a mixture of tetrasodium pyrophosphate and sodium acid pyrophosphate resulted in significant reductions in tartar accumulation. The aqueous solutions containing 1.5 and 0.5 weight percent of a mixture of tetrasodium pyrophosphate and sodium acid pyrophosphate resulted in directional trends of reductions in tartar accumulation. See also U.S. Pat. No. 3,323,551.

The ratio of sodium acid pyrophosphate (SAPP) to tetrapotassium pyrophosphate (TKPP) is generally between 4 to 1 and 3 to 7, preferably between 7 to 3 and 1 to 1, most preferably about 3 to about 2. SAPP has a pH of 4.2 and TKPP (and TSPP) has a pH of 10.2, so the combination of SAPP and TKPP (or TSPP) provides a resultant pH which is a balance of the pHs of the two components.

The pH of the dough of at least one inorganic pyrophosphate compound (salt) is generally in the range of about 4 to about 10.5, typically from about 4.5 to about 7.5, preferably from about 5 to about 7, most preferably between about 5.6 and 6.0. Milk Bone ® dog biscuit has a pH of 6.1 to 6.4. Tartar reduction is indicated to be best at neutral pH and palatability is indicated to be best at a slightly acidic pH, so the best mode contemplates a balance of such two factors.

The dough ingredient is generally mixed at a temperature of about 45° to about 140° F., preferably about 60° to about 125° F.

The dough can also contain suitable surfactants or emulsifying agents, e.g., cationic agents and nonionic agents. Suitable nonionic emulsifying agents can be broadly defined as compounds produced by the condensation of alkylene oxide groups (hydrophilic in nature) with an organic hydrophobic compound which can be aliphatic, alkyl aromatic, or a condensate of an alkylene oxide with an alkylene glycol in nature. Examples of suitable nonionic emulsifying agents include the Piuronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulphoxides, and mixtures of such materials. The emulsifier is best used in minor amounts.

The dog biscuit dough can be mixed using any suitable or conventional equipment. For example, the mixing can be at 20 to 100 rpm. For example, a dry blending step (dries and the inorganic pyrophosphates) can be done typically at room temperature for a period of time of about 3 minutes to about 20 minutes. The dry-blended mixture can then be mixed with the hot water to form a first stage dough. The water which can be admixed with the dry-blended mixture is typically at a temperature of about 65° to about 150° F. The hot water can be added, with mixing, over a period of time of about 3 minutes to about 6 minutes to form the first stage dough. Then, the fat portion of the biscuit dough can be admixed with the first stage dough to form the final stage dough. The fat portion can be added at a temperature at which it is at least fluid, typically at about 100° to about 150° F. The fat portion can be mixed for a period of time which is sufficient to form a dough whose homogeneity is visually apparent. A typically final mixing time is about 3 to about 5 minutes.

If there are machinability and dough structure property problems with the invention dough, the addition of water should solve such problems. If the use of the higher water levels causes the dough to be so sticky as to cause problems in a sigma or rotary mixer (but normally not a significant problem in a continuous mixer). The addition of more tallow to the dog biscuit dough should assist in more effective mixing and help to keep the dough from being so sticky that it clings to the rotary molder. Preferably the tallow level is about 2.6 to about 3.1 weight percent (most preferably about 2.85 weight percent), as opposed to a tallow level of about 2.46 weight percent in Milk Bone ® dog biscuits. Also, the tallow provides a taste which dogs like.

Formation of the dough is achieved at about atmospheric pressure with mixing of the components being conveniently achieved in an upright sigma blade mixer or other bakery-type mixers. The various ingredients can be added over a period of time or in a one-shot manner according to the above order of addition. However, melted fat and water can be added simultaneously and mixed for 6 to 10 minutes.

The dog biscuits are formed in any conventional or suitable manner, such as, by extrusion, stamping, cutting or molding. Any suitable dog biscuit shapes can be used, such as, a bone-shaped canine biscuit. For many products, such as, the bone-shaped canine biscuits of the invention, a rotary molding system is preferred because it permits the rapid forming of dough pieces with good control over their shape, form and surface characteristics. Docker holes are preferably formed in the dough piece during molding to facilitate the escape of moisture during baking.

The dough can then be formed into pieces by machining on a rotary molder with specific die shapes. The dough can also be formed into pieces by sheeting followed by either a vertical or rotary cutter or by a rotary molder. Suitable die and cutter shapes are those which result in a round, square, triangular, T-bone or chop-shaped biscuit product and the like. The forming is achieved at conventional temperatures of ambient to 110° F. and pressures of less than 75 p.s.i. (gauge), used with a rotary molder, a vertical cutter or rotary cutter.

The dough pieces can be baked using any suitable or conventional equipment and conditions. For example, the dough pieces can be passed into an oven such as a conventional band oven where the biscuit is baked. The conveyer belts of the oven can be coated with an edible lubricant such as a natural or synthetic cooking oil or shortening to facilitate separation from the conveyer belts of the baked products. Temperatures in the range of about 300° to about 600° F. can be used. The baked biscuits can also be subjected to subsequent drying at temperatures of about 200° to 400° F., either within the baking oven or separately, to produce the desired moisture content in the final product.

The formed pieces are baked, followed by drying, to achieve a shelf stable product without the need of any moisture barrier protection. Baking and drying temperatures and times are those conventionally used in the production of a hard, dry canine biscuit. The pieces are dried to obtain a biscuit having a water activity of 0.70 or less. Typically, baking temperatures and times are about 300° F to about an average of 475° F. for about 25 minutes to about 8 minutes. Drying conditions are typically about 200° to about 325° F. for about 25 minutes to about 12 minutes in a forced air dryer. On a weight basis, the moisture content of the final biscuit product is less than or equal to about 15 percent by weight and preferably about 10 to 12 percent by weight of the final biscuit at 70 percent relative humidity.

The ingredients, pH and ranges for the invention dough are the same for the invention dog biscuits.

The invention product is generally as palatable as Milk Bone ® biscuits, which have been widely accepted and a commercial success for many years.

The invention product does not include any fluorine-containing compound or other fluoride ion source, or quaternary ammonium compounds. Also the invention product does not include any organic pyrophosphates.

The invention deals primarily with dogs, but has a scope of teeth-bearing non-human mammals, such as, cats.

The invention composition is used to reduce and control tartar accumulation on canine teeth. Based upon the weight of commercial Milk Bone ® dog biscuits: 12 small invention dog biscuits per day, 10 medium invention dog biscuits per day, 6 large invention dog biscuits per day or 4 extra large invention dog biscuits per day will supply about ¼ to ⅓ of a dog's caloric requirement.

The following is a summary of experiments described in more detail below:

Example 1: Initial testing of solutions of pyrophosphates. Solutions were applied directly to teeth.

Example 2: Addition of pyrophosphate (5 percent delivered) to Milk Bone ® formula. Milk Bone ® is a registered trademark of Nabisco Brands, Inc. for canine biscuits.

Example 3 Dose response study. Pyrophosphate at 0.5, 1.5, 3.0 and 5.0 percent delivered were added to the Milk Bone ® formula.

Examples 2 and 3 are based upon modifications of the formula of Milk Bone ® dog biscuits.

TABLE 1

TARTAR CONTROL BISCUITS
SUMMARY OF FORMULA DEVELOPMENT

| Ingredients | Control Regular Milk Bone ® Lbs. | Ex. 2 5% Pyro-Phosphate Lbs. | Ex. 3 Dose Study. Lbs. |
|---|---|---|---|
| Flour | 940.000 | 940.000 | See Example 3 |
| Soybean Meal | 135.000 | 135.000 | |
| Meat & Bone Meal | 100.000 | 100.000 | |
| Wheat Meal | 40.000 | 40.000 | |
| Tallow | 32.000 | 32.000 | |
| Salt | 10.000 | 10.000 | |
| Dicalcium Phosphate | 8.500 | 8.500 | |
| Natural Flavorants | 17.000 | 17.000 | |
| Bone Meal | 5.000 | 5.000 | |
| Calcium Carbonate | 2.000 | 2.000 | |
| Dough Conditioners | 2.875 | 2.875 | |
| Vitamin Premix | 0.375 | 0.375 | |
| Tetrasodium Pyrophosphate | 0 | 70.280 | |
| Sodium Acid Pyrophosphate | 0 | 23.450 | |
| Tetrapotassium Pyrophosphate | 0 | 0 | |
| Calcium | 0 | 0 | |
| TOTAL | 1,292.750 | 1,386.48 | |

EXAMPLE 1

Solution Tests

Purpose

To determine the dose response of three concentrations of an anti-tartar agent (pyrophosphate) to reduce accumulation of tartar formation in the dog.

Test Design

Treatment

DI $H_2O$-Control
3.3% Pyrophosphate
5.0% Pyrophosphate
6.7% Pyrophosphate

Test Solutions

Formulas

| Tetrasodium Pyrophosphate (TSPP) | Sodium Acid Pyrophosphate (SAPP) | % Delivered Pyrophosphate |
|---|---|---|
| 3.58 grams | 1.22 grams | 3.3 |
| 5.42 grams | 1.85 grams | 5.0 |
| 7.27 grams | 2.48 grams | 6.7 |

The above pyrophosphates were mixed with 100 ml of DI $H_2O$. The test solutions were applied to the teeth using a modified syringe. The ratio of the above blends of TSPP and SAPP is: TSPP-75 percent, SAPP-25 percent.

pH of Test Solutions

| Test Solutions | pH |
|---|---|
| 3.3% | 7.92 |
| 5.0% | 7.74 |
| 6.7% | 7.85 |

Results

A significant reduction in tartar accumulation was shown with the 5 percent pyrophosphate solution.

EXAMPLE 2

Pilot Plant Study With Milk Bone ®Containing 5 Percent of Deliverable Pyrophosphate

Purpose

The addition of pyrophosphate to Milk Bone ® dog biscuits.

Test

Tetrasodium pyrophosphate (TSPP) and sodium acid pyrophosphate (SAPP) were used. The ratio of the pyrophosphates was 75 percent of TSPP and 25 percent of SAPP. The level of TSPP was 5.1 percent and SAPP was 1.69 percent of the formula weight—which delivers approximately 5.0 percent of pyrophosphate. The TSPP and SAPP, dissolved in water, were just added to the total weight of the regular Milk Bone ® formula. No other formula adjustments were made so that the effects of the pyrophosphates could be determined.

The study originally was designed to test Milk Bone ® with 5.0, 7.5 and 10.0 percent of deliverable pyrophosphate. At the 7.5 and 10.0 percent levels, acceptable biscuits could not be rotary molded. The finished product was extremely soft and had distorted shapes. Biscuits with 5.0 percent of pyrophosphate were borderline acceptable. The color of the biscuits were whitish in color, whereas the control biscuits are tan/-beige in color.

Results

A significant reduction in the accumulation of tartar was seen at the 5 percent pyrophosphate level. There was a significant amount of breakage (30 to 35 percent) with the 5 percent pyrophosphate biscuits.

Additional Information pH of biscuits:
Control Milk Bone ®—6.15
5 percent of pyrophosphate Milk Bone ®—6.98

EXAMPLE 3

Pilot Plant Dose Response Study

Purpose

To establish a dose level which is effective for tartar control.

Test

The TSPP and SAPP solutions were added to the weight of the regular Milk Bone ® formula. No other formula adjustments were made so that the effect of the pyrophosphates could be determined. The pyrophosphates were dissolved in water (135° to 140° F.) and added to the Milk Bone ® dries. Regular medium Milk Bone ® and four medium Milk Bone ® test products were made. Each of the test products contained different levels, 0.5, 1.5, 3.0 and 5.0 percent of deliverable pyrophosphates. The ratio of the blend of tetrasodium pyrophosphate (TSPP) and sodium acid pyrophosphate (SAPP) was:

| TSPP | 75% | for all four levels |
|------|-----|---------------------|
| SAPP | 25% | |

The total amounts of TSPP and SAPP added to the formula and approximate delivered soluble pyrophosphate ($P_2O_7$) were:

|  | % | % | % | % |
|---|---|---|---|---|
| (75%) TSPP added | 0.54 | 1.60 | 3.17 | 5.10 |
| (25%) SAPP added | 0.18 | 0.53 | 1.10 | 1.69 |
| Total | 0.72 | 2.13 | 4.27 | 6.79 |
| Approx. delivery of soluble pyrophosphate | 0.5% | 1.5% | 3.0% | 5.0% |

Pilot Plant Trials

The doughs containing 0.5 and 1.5 percent of delivered pyrophosphates were similar in development to control regular Milk Bone ® dog biscuits. However, the doughs with the 3 and 5 percent levels were shorter in texture and not as developed as the control. The finished products at these two levels were less hard than the control biscuits.

pH—of Biscuits (10% solution)

|  | pH |
|---|---|
| Regular Milk Bone ® | 6.10 |
| 0.5% biscuits | 6.41 |
| 1.5% biscuits | 6.75 |
| 3.0% biscuits | 6.88 |
| 5.0% biscuits | 7.07 |

Results of the Study

| Pyrophosphate Delivery | Results |
|---|---|
| 0.5% Milk Bone ® biscuits | No significant reduction in tartar accumulation directional trend |
| 1.5% Milk Bone ® biscuits | No significant reduction in tartar accumulation directional trend |
| 3.0% Milk Bone ® biscuits | A significant reduction in tartar accumulation |
| 5.0% Milk Bone ® biscuits | A significant reduction in tartar accumulation |

A significant amount of breakage (approx. 25 percent) was reported for the 5 percent pyrophosphate biscuits. There was approximately 15 percent breakage with the 3 percent level. At the 0.5 and 1.5 percent of pyrophosphate levels, the breakage was not considered excessive compared to the control biscuits.

Test data and results are set out in the following table:

TABLE 2

REGULAR MILK BONE ®/PYROPHOSPHATE/TARTAR CONTROL DOSE RESPONSE STUDY

| | CONTINUOUS | PYRO-PHOSPHATE | PYRO-PHOSPHATE |
|---|---|---|---|

TABLE 2-continued

REGULAR MILK BONE ®/PYROPHOSPHATE/TARTAR CONTROL
DOSE RESPONSE STUDY

| INGREDIENTS | MIX CONTROL LBS | PERCENT | .50% Lbs. | PERCENT | 1.50% Lbs. | PERCENT |
|---|---|---|---|---|---|---|
| Flour | 940.00 | 72.7132 | 940.00 | 72.1855 | 940.00 | 71.1604 |
| Soy Meal | 135.00 | 10.4429 | 135.00 | 10.3671 | 135.00 | 10.2198 |
| Meat & Bone Meal | 100.00 | 7.7354 | 100.00 | 7.6793 | 100.00 | 7.5703 |
| Wheat Meal | 40.00 | 3.0942 | 40.00 | 3.0717 | 40.00 | 3.0281 |
| Tallow | 32.00 | 2.4753 | 32.00 | 2.4574 | 32.00 | 2.4225 |
| Salt | 10.00 | 0.7735 | 10.00 | 0.7679 | 10.00 | 0.7570 |
| Dicalcium Phosphate | 8.50 | 0.6575 | 8.50 | 0.6527 | 8.50 | 0.6435 |
| Natural Flavorants | 17.00 | 1.3157 | 17.00 | 1.3056 | 17.00 | 1.2869 |
| Bone Meal | 5.00 | 0.3868 | 5.00 | 0.3840 | 5.00 | 0.3785 |
| Calcium Carbonate | 2.00 | 0.1547 | 2.00 | 0.1536 | 2.00 | 0.1514 |
| Dough Conditioners | 2.875 | 0.2224 | 2.875 | 0.2208 | 2.875 | 0.2176 |
| Vitamin Premix | 0.375 | 0.0290 | 0.375 | 0.0288 | 0.375 | 0.0284 |
| Tetrasodium Pyrophosphate | 0 | 0 | 7.07 | 0.5429 | 21.14 | 1.6003 |
| Sodium Acid Pyrophosphate | 0 | 0 | 2.38 | 0.1828 | 7.07 | 0.5352 |
| TOTAL | 1,292.75 | | 1,302.2 | | 1,320.96 | |

| INGREDIENTS | PYROPHOSPHATE 3.0% Lbs. | PERCENT | PYROPHOSPHATE 5.0% Lbs. | PERCENT |
|---|---|---|---|---|
| Flour | 940.00 | 69.6797 | 940.00 | 67.7976 |
| Soy Meal | 135.00 | 10.0072 | 135.00 | 9.7369 |
| Meat & Bone Meal | 100.00 | 7.4127 | 100.00 | 7.2125 |
| Wheat Meal | 40.00 | 2.9651 | 40.00 | 2.8850 |
| Tallow | 32.00 | 2.3721 | 32.00 | 2.3080 |
| Salt | 10.00 | 0.7413 | 10.00 | 0.7213 |
| Dicalcium Phosphate | 8.50 | 0.6301 | 8.50 | 0.6131 |
| Natural Flavorants | 17.00 | 1.2601 | 17.00 | 1.2261 |
| Bone Meal | 5.00 | 0.3706 | 5.00 | 0.3606 |
| Calcium Carbonate | 2.00 | 0.1483 | 2.00 | 0.1443 |
| Dough Conditioners | 2.875 | 0.2132 | 2.875 | 0.2074 |
| Vitamin Premix | 0.375 | 0.0278 | 0.375 | 0.0270 |
| Tetrasodium Pyrophosphate | 42.210 | 3.1289 | 70.28 | 5.0689 |
| Sodium Acid Pyrophosphate | 14.070 | 1.0430 | 23.45 | 1.6913 |
| TOTAL | 1,349.03 | | 1,386.48 | |

Definitions

SAPP is sodium acid pryophosphate.
TSPP is tetrasodium pyrophosphate.
TKPP is tetrapotassium pyrophosphate.

What is claimed is:

1. A baked dog or cat biscuit which comprises a tartar-reduction effective amount of at least one metal inorganic phosphate of the formula $M_{n+2}P_nO_{3n+1}$, wherein M is a univalent metal and n is 2, 3, 4 or 5, or of the formula $M'_nP_nO_{3n+1}$, where M' is a divalent metal and n has the above meaning, said at least one metal phosphate having an oxide ratio of cationic oxides ($M_2O$ or $M'O$) and anionic oxides ($P_2O_5$) being between 1 and 2 or being 2.

2. A baked dog or cat biscuit as claimed in claim 1 wherein the baked dog or cat biscuit contains about 0.1 to about 10 weight percent of said at least one metal inorganic phosphate.

3. A baked dog or cat biscuit as claimed in claim 2 wherein the baked dog or cat biscuit has a moisture content of about 5 to about 15 weight percent.

4. A baked dog or cat biscuit as claimed in claim 1 wherein the baked dog or cat biscuit contains about 0.5 to about 5 weight percent of said at least one metal inorganic phosphate.

5. A baked dog or cat biscuit as claimed in claim 2 wherein the at least one metal inorganic phosphate is an alkali metal pyrophosphate.

6. A baked dog or cat biscuit as claimed in claim 2 wherein the at least one alkali metal inorganic pyrophosphate is tetrasodium pyrophosphate.

7. A baked dog or cat biscuit as claimed in claim 2 wherein the at least one metal inorganic phosphate is a combination of trisodium monoacid pyrophosphate and tetrapotassium pyrophosphate or tetrasodium pyrophosphate.

8. A baked dog or cat biscuit as claimed in claim 2 wherein the at least one metal inorganic phosphate has the formula $M_{n+2}P_nO_{3n+1}$, and the oxide ratio of cationic oxides and anionic oxides is between 1 and 2.

9. A baked dog or cat biscuit as claimed in claim 1 wherein the baked dog biscuit is bone shaped.

10. A baked dog or cat biscuit as claimed in claim 1 wherein the at least one metal inorganic phosphate has the formula $M_{n+2}P_nO_{3n+1}$, and the oxide ratio of cationic oxides and anionic oxides is between 1 and 2.

11. A baked dog or cat biscuit as claimed in claim 10 wherein n is 3.

12. A baked dog or cat biscuit as claimed in claim 2 wherein the at least one metal inorganic phosphate is an alkaline earth pyrophosphate.

13. A baked dog or cat biscuit comprising about 0.1 to about 10 weight percent of at least one alkali metal inorganic pyrophosphate, the baked dog or cat biscuit having a moisture content of about 5 to about 15 weight percent, based upon the total weight of the baked dog or cat biscuit, said at least one alkali metal inorganic pyrophosphate being water soluble, the baked dog or cat biscuit being slightly acid to neutral, and the dog biscuit having a water activity of 0.70 or less.

14. A baked dog or cat biscuit as claimed in claim 13 wherein the at least one alkali metal inorganic pyrophosphate is tetrasodium pyrophosphate.

15. A baked dog or cat biscuit as claimed in claim 13 wherein the at least one alkali metal inorganic pyrophosphate is a combination of trisodium monoacid pyrophosphate and tetrapotassium pyrophosphate.

* * * * *